United States Patent [19]
Schwartz

[11] Patent Number: 5,093,234
[45] Date of Patent: Mar. 3, 1992

[54] METHOD OF ALIGNING, COMPENSATING, AND CALIBRATING A FLOW CYTOMETER FOR ANALYSIS OF SAMPLES, AND MICROBEAD STANDARDS KIT THEREFOR

[75] Inventor: Abraham Schwartz, Durham, N.C.

[73] Assignee: Caribbean Microparticles Corporation, Hato Rey, P.R.

[21] Appl. No.: 374,435

[22] Filed: Jun. 30, 1989

Related U.S. Application Data

[63] Continuation-in-part of Ser. No. 128,786, Dec. 4, 1987, Pat. No. 4,857,451, which is a continuation-in-part of Ser. No. 805,654, Dec. 11, 1985, Pat. No. 4,774,189, which is a continuation-in-part of Ser. No. 685,464, Dec. 24, 1984, Pat. No. 4,767,206.

[51] Int. Cl.$^5$ .............. G01N 33/53; G01N 31/00; G01N 33/48; G01J 3/30
[52] U.S. Cl. .............. 435/7.21; 435/967; 436/8; 436/10; 436/800; 436/63; 436/808; 356/318; 356/441; 356/213; 356/243
[58] Field of Search .............. 436/8–18, 436/63, 800, 808; 435/967, 7.21; 422/82.08; 356/318, 213, 243, 441

[56] References Cited

U.S. PATENT DOCUMENTS

| | | | |
|---|---|---|---|
| 4,162,282 | 7/1979 | Fulwyler et al. | 436/10 |
| 4,767,206 | 8/1988 | Schwartz | 436/10 |
| 4,774,189 | 9/1988 | Schwartz | 436/10 |
| 4,857,451 | 8/1989 | Schwartz | 436/10 |

*Primary Examiner*—David L. Lacey
*Assistant Examiner*—William Chan
*Attorney, Agent, or Firm*—Olive & Olive

[57] ABSTRACT

A kit of highly uniform size microbead standards for flow cytometer alignment, compensation, and/or calibration, comprising a blank microbead population and/or an auto-fluorescent microbead population, together with two or more series of calibrated microbead populations labeled with fluorescent dye(s) which (i) prior to fluorescent dye(s) labeling, match the fluorescence spectra and fluorescence intensity of the blank and/or autofluorescent microbead population, and (ii) after fluorescent dye(s) labeling, match the fluorescence spectra and fluorescence intensity of fluorescently labeled samples to be measured on the flow cytometer. Also disclosed is a corresponding method to align, compensate, and/or calibrate a flow cytometer so as to make measurements on samples comparable and independent of the specific instrument and instrument settings.

29 Claims, 2 Drawing Sheets

METHOD OF ALIGNING, COMPENSATING, AND CALIBRATING A FLOW CYTOMETER FOR ANALYSIS OF SAMPLES, AND MICROBEAD STANDARDS KIT THEREFOR

CROSS-REFERENCE TO RELATED APPLICATIONS

This application is a continuation-in-part of U.S. application Ser. No. 07/128,786 filed Dec. 4, 1987, issued Aug. 15, 1989, as U.S. Pat. No. 4,957,451, which in turn is a continuation-in-part of U.S. application Ser. No. 06/805,654 filed Dec. 11, 1985, issued Sept. 27, 1988 as U.S. Pat. No. 4,774,189, which in turn is a continuation-in-part of U.S. application Serial No. 685,464 filed Dec. 24, 1984, issued Aug. 30, 1988 as U.S. Pat. No. 4,767,206.

BACKGROUND OF THE INVENTION

1. Field of the Invention

This invention relates generally to a method for aligning, compensating, and/or calibrating a multiple fluorescent channel flow cytometer for subsequent analysis of samples, and to a kit of fluorescent microbeads useful for such method.

2. Background and Description of the Art

Flow cytometers are instruments which analyze biological cells and particles in a thin stream of fluid intersected by an illumination source, usually a laser beam, with the resulting forward and right angle scattered and fluorescent light analyzed with photomultiplier tubes (PMTs). Fluorescent channels are usually indicated by the designations F11, F12, F13, etc., depending on the number of channels in the instrument Each fluorescent channel is set with barrier filters to detect a selected specific dye while filtering out all others. The channel in which a specific dye is predominantly detectable may be referred to as its primary fluorescent channel while other fluorescent channels may be designated as secondary channels.

In order to obtain accurate and reproducible results, flow cytometers must be aligned and calibrated. When operation with more than one fluorescent dye, the instrument also requires compensation for the fluorescence PMTs. Alignment, compensation, and calibration ensure that the instrument will operate at its maximum efficiency, as well as achieving reproducibility such that data taken over time or with various instruments will be comparable.

Alignment is the process of adjusting and focusing the various optical and electrical components such that scatter and fluorescence signals are tuned to their highest intensity and tightest distribution, i.e., lowest coefficient of variation (CV) of the distribution. The components of the flow cytometer to be aligned include the laser, lenses, mirrors, barrier filters, and PMTs FIG. 1 shows what the dot plot of the forward and right angle scatter channels typically looks like when the instrument is not aligned The corresponding dot plot of FIG. 2 indicates proper alignment of those channels Compensation is the process of electronically removing residual signals from fluorescent dyes in secondary fluorescence channels due to spectral overlaps not removed by the barrier filters for the respective channels When compensation circuits are turned off, the dot plot for the fluorescent channel F11 versus the fluorescent channel F12 appears as in FIG. 3, with fluorescent microbeads (2) and (3) overlapping the boundaries designated by blank microbeads (1). The dot plot of FIG. 4 shows that the compensation circuits are adjusted properly so that the intensity of any signal in the secondary fluorescent channels is equivalent to the blank samples. In other words, the dot group must be aligned with a blank or unlabeled sample in the secondary fluorescence channel. If this is not accomplished, the samples labeled with a single fluorescent dye will be counted in both fluorescent channels when it should only be counted in its respective primary fluorescent channel. In addition, if the compensation is set too high, as illustrated in FIG. 5, then data from the sample may be lost.

Multi-fluorescence analysis, i.e., analysis using two or more fluorescent dyes simultaneously, can be performed on a flow cytometer. However, to perform accurate analysis, it is necessary to adjust the electrical compensation circuits in the flow cytometer such that any fluorescence emission which overlaps into other fluorescence channels may be subtracted from such other channels As an example, using fluorescein and phycoerythrin as simultaneously employed fluorescent dyes, the green fluorescence channel for fluorescein may have a band pass emission filter of $520 \pm 10$ nanometers (nm) and the red fluorescence channel for phycoerythrin may have a band pass emission filter of $580 \pm 10$ nm. The emission spectra of fluorescein is such that part of its fluorescence will be seen in the phycoerythrin fluorescence channel of $580 \pm 10$ nm, and to a lesser degree, part of the emission of phycoerythrin will appear in the fluorescein fluorescence channel of $520 \pm 10$ nm.

A particular problem associated with numerous samples measured by flow cytometry relates to naturally occurring fluorescence, i.e., autofluorescence, of the sample. For example, a wide variety of biological cells contain naturally occurring fluorescent compounds such as riboflavin. Such autofluorescence introduces an additional complexity to the flow cytometer compensation process, and tends to promote mis-compensation (over- and/or under-compensation) in the respective fluorescence channels of the flow cytometer.

Calibration of a flow cytometer with proper standards ensures that the results from samples will be comparable over time and between different instruments. For the calibration of the intensity of fluorescence signals to be independent of the specific instrument and instrument settings, the excitation and emission spectra of the calibration standards and of the samples being measured must be equivalent and the measurements on each must be made under the same instrument settings. In addition, as described in U.S. Pat. Nos. 4,714,682; 4,767,206; and 4,774,189, and copending U.S. application Ser. No. 109,214, the disclosures of which hereby are incorporated by reference, when the calibration is made in terms of number of equivalent soluble fluorescent molecules, such correction factors as quenching and changes in extinction coefficient due to conjugation to other molecules, need not be taken into consideration.

Fluorescence calibration curves for flow cytometers may be constructed by plotting the mean or modal channels of the fluorescence intensity histograms of fluorescence microbead standards against the calibrated values of the number of equivalent soluble fluorescent dye molecules for the respective microbead standards, as shown in FIG. 6.

Small (0.1-2 microns) highly uniform microbeads are readily commercially available from a number of manufacturing companies, e.g., Seragen, Inc., Polysciences, Inc., and Interfacial Dynamics Corp. Production of large (2-50 microns) highly uniform microbeads are described in U.S. Pat. Nos. 4,247,434 and 4,336,173. The synthesis of fluorescent microbeads is taught in U.S. Pat. Nos. 4,157,323 and 4,179,685, but these microbeads are not intended to be used as uniform standards and their spectra are not designed to match those of labeled samples.

The aforementioned U.S. Pat. Nos. 4,714,682; 4,767,206; and 4,774,189, and copending application Ser. No. 109,214 relate to calibration of flow cytometers in terms of equivalent soluble fluorescent dye molecules with standards (calibration microbeads) that have matching fluorescent properties.

A kit of microbeads that match labeled cells is commercially available under the trademark CaliBrites from Becton Dickinson & Co. (Mountain View, California), which consists of three microbead populations: (i) an unlabeled population, (ii) a fluorescein-labeled population, and (iii) a phycoerythrin-labeled population. None of these microbeads are calibrated in any way, and they are intended only for alignment and compensation of a flow cytometer.

It is therefore an object of the present invention to provide a method for alignment, compensation, and/or calibration of a flow cytometer for analysis of selected samples which may comprise, in a specific aspect of the invention, naturally fluorescent samples), enabling the flow cytometer to operate at high efficiency with respect to fluorescence data generated thereby, and in a manner achieving reproducibility of data which is independent of the specific instrument and time-frame of the data measurement.

It is another object of the invention to provide a microbead standards kit for carrying out such alignment, compensation, and calibration method.

Other objects and advantages of the invention will be more fully apparent from the ensuing disclosure and appended claims.

SUMMARY OF THE INVENTION

The present invention relates in one aspect to a method of aligning, compensating, and/or calibrating a flow cytometer, for subsequent measurement of a selected sample which is labeled with fluorescent dyes for measurement of the sample in multiple fluorescence channels of the flow cytometer. The invention relates in another aspect to a kit useful for carrying out such method, which contains several series of highly uniform size microbeads (i.e., $\leq 2\%$ coefficient of variation of diameter).

The kit aspect of the invention kit broadly relates to a microbead standards kit for alignment, compensation, and/or calibration of a flow cytometer, for subsequent measurement of a selected sample which is labeled with fluorescent dyes for measurement of the sample in multiple fluorescence channels of the flow cytometer. Such kit comprises:

(a) a first population of microbeads with a same fluorescence spectra and fluorescence intensity as a selected sample, prior to the selected sample being labeled with fluorescent dyes to provide a fluorescently labeled sample for flow cytometry measurement, such first population of microbeads being selected from the group consisting of (i) non-fluorescent microbeads, and (ii) autofluorescent microbeads, for use when the sample is naturally fluorescent, labeled with a first fluorescence component to mimic the fluorescence spectra and fluorescence intensity of the sample prior to its labeling with fluorescent dyes;

(b) additional populations of microbeads which are fluorescently labeled with at least two fluorescent dyes and which prior to being thus fluorescently labeled are characterized by a same fluorescence spectra and fluorescence intensity as the first microbeads population (a), such that the additional microbead populations comprise microbeads which are characterized by fluorescence intensity levels registerable in multiple fluorescent channels of a flow cytometer, each same additional population of microbeads comprising a series of sub-populations of such microbeads characterized by differing selected levels of fluorescence intensity to substantially encompass, either directly or by extrapolation, a range of fluorescence intensity of the fluorescently labeled sample to be measured by the flow cytometer, when the fluorescently labeled sample is fluorescently labeled with same fluorescent dye(s);

(c) the microbead populations (a) and (b) being constituted by highly uniform same sized microbeads having a coefficient of variation of diameter of about 2% or less, with the microbeads being substantially equivalent in size to the fluorescently labeled sample to be measured by the flow cytometer; and (d) container means enclosing the microbead populations (a) and (b).

In a specific embodiment, the kit is adapted for aligning, compensating, and calibrating a flow cytometer for subsequent measurement of a selected naturally fluorescent sample which is labeled with fluorescent dyes. In this embodiment, the kit comprises a first population of microbeads (a) which is fluorescently labeled with a first fluorescence component so that the first population microbeads are characterized by a same fluorescence spectra and fluorescence intensity as the selected naturally fluorescent sample, prior to such sample being labeled with fluorescent dye(s) to provide a fluorescently labeled sample for flow cytometry measurement.

In this specific embodiment, the kit comprises additional populations of microbeads (b) which are fluorescently labeled with the first fluorescence component and are further labeled with at least two fluorescent dyes different from the first fluorescence component, such that the additional microbead populations comprise microbeads which are characterized by fluorescence intensity levels registerable in multiple fluorescent channels of the flow cytometer. Each same additional population comprises a series of sub-populations of the microbeads which are characterized by differing selected levels of fluorescence intensity, to substantially encompass, either directly or by extrapolation, a range of fluorescence intensity of the fluorescently labeled sample to be measured by the flow cytometer, when the fluorescently labeled sample is fluorescently labeled with same fluorescent dye(s).

In a further specific aspect, the additional microbead populations (b) comprise a first sub-population comprising microbeads labeled with a first fluorescent dye, and a second sub-population comprising microbeads labeled with a second fluorescent dye.

In another specific aspect, the additional microbead populations (b) comprise microbeads which are multiply labeled with different fluorescent dyes.

With such kit, the series of microbeads may be used to align, compensate, and calibrate the respective primary fluorescence channels of the flow cytometer for the fluorescent dyes employed for fluorescently labeling the sample to be measured by the flow cytometer. The general size and fluorescence properties of the individual microbead populations of these series of microbeads are as described in U.S. Pat. Nos. 4,714,682; 4,767,206; and 4,774,189. The specific fluorescence properties of the first population (a) of microbeads, i.e., non-fluorescent ("blank") microbeads and/or "autofluorescent" microbeads which are fluorescently labeled with a first fluorescent component, and the additional populations (b) of microbeads which are fluorescently labeled with at least two fluorescent dyes and which prior to such fluorescent labeling match the fluorescence spectra and fluorescence intensity of the first population (a) microbeads, as included in the microbeads standards kit of the present invention, will be described more fully hereinafter.

When used separately or in combinations, the microbead populations in this kit will allow the flow cytometer to be aligned (due to the high uniformity of the microbeads,) compensated (due to the matching emission of the microbead standards and the cell or particle samples to be measured), and calibrated (due to the specific levels of fluorescence intensity of the microbeads in terms of number of equivalent soluble fluorescent dye molecules). These operations will enable the instrument to yield accurate reproducible data so that fluorescence intensity measurements made thereafter on the flow cytometer will not require correction factors due to quenching or change in extinction coefficient.

DETAILED DESCRIPTION OF THE INVENTION, AND PREFERRED EMBODIMENT THEREOF

Figure 1:
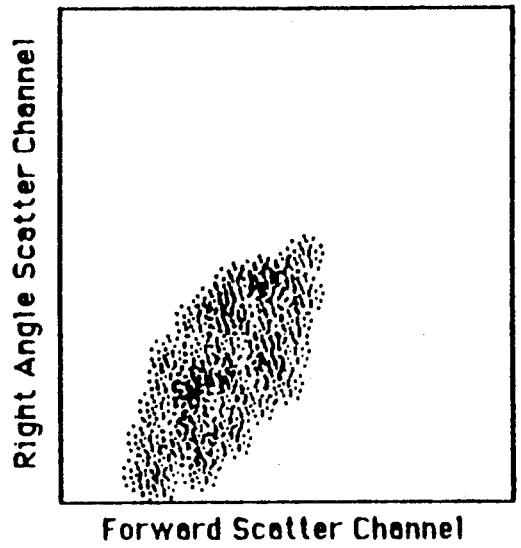
FIG. 1 is a forward versus right angle dot plot for a flow cytometer which is not aligned.
Figure 2:
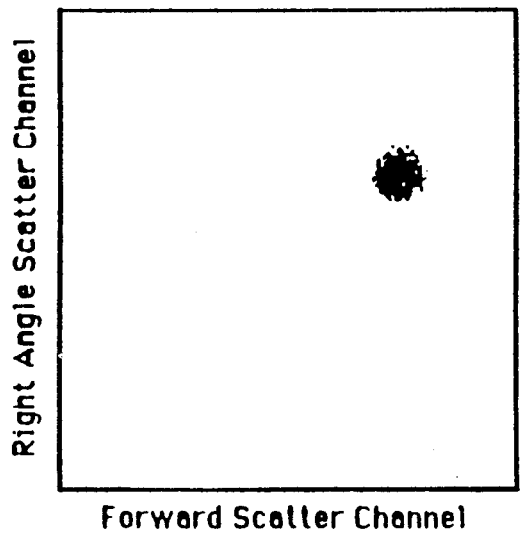
FIG. 2 is a forward versus right angle dot plot for a flow cytometer which is aligned.
Figure 3:
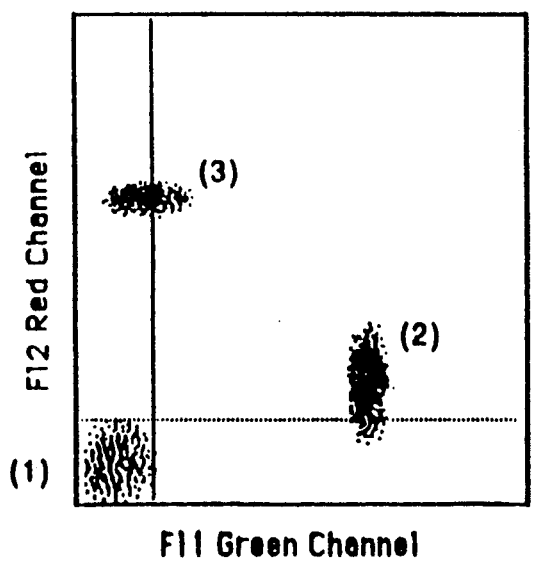
FIG. 3 is a dot plot of the green fluorescence channel F11 versus the red fluorescence channel F12 of a flow cytometer with its compensation circuits turned off. Dot populations represent (1) blank microbeads, (2) green fluorescent microbeads, and (3) red fluorescent microbeads, as do the same parenthetic numbers in FIGS. 4-5.
Figure 4:
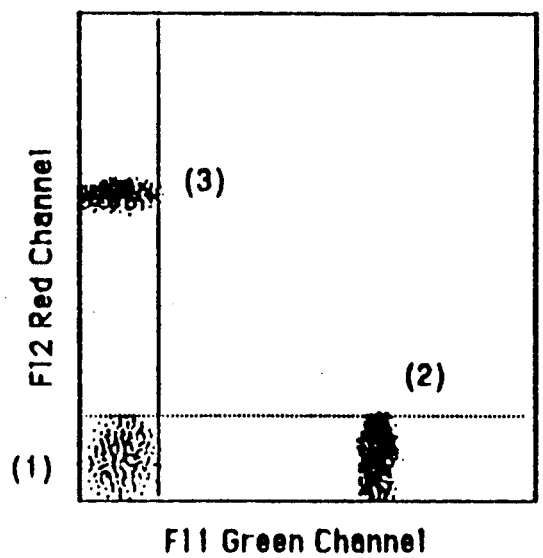
FIG. 4 is a dot plot of the green fluorescence channel F11 versus the red fluorescence channel F12 of a flow cytometer with its compensation circuits turned on and properly adjusted.
Figure 5:
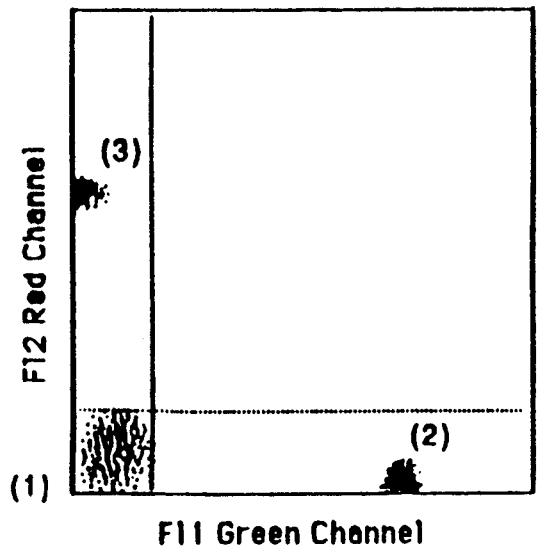
FIG. 5 is a dot plot of the green fluorescence channel F11 versus the red fluorescence channel F12 of a flow cytometer with its compensation circuits adjusted too high, resulting in loss of data or inaccurate data from the samples being measured.

The microbead standards kit useful in the broad practice of the present invention will contain (a) a first population of microbeads selected from the group consisting of (i) non-fluorescent microbeads, and (ii) autofluorescent microbeads, i.e., microbeads which are fluorescently labeled with a first fluorescence component to mimic the naturally occurring fluorescence (i.e., fluorescence spectra and fluorescence intensity) of an autofluorescent sample which is to be fluorescently dyed and measured on the flow cytometer, and (b) at least two different series of calibrated fluorescent microbead populations which are fluorescently labeled with at least two fluorescent dyes (different from the first fluorescence component) and which prior to being fluorescent dye labeled are characterized by a same fluorescence spectra and fluorescence intensity as population (a) microbeads.

By means of this kit, the alignment, compensation, and calibration of multi-fluorescence channels of a flow cytometer are readily carried out, for subsequent measurement of a selected sample which is labeled with fluorescent dyes, in multiple fluorescence channels of the flow cytometer.

The microbeads in both respective populations (a) and (b) of the microbead standards kit, prior to the labeling of the population (b) microbeads with the dye(s) employed to stain the sample to be measured on the flow cytometer, must be characterized by the same "noise" and/or fluorescence (spectra and intensity) characteristics. "Blank" or non-fluorescent microbeads are employed in the population (a) microbeads when the sample to be measured by the flow cytometer is itself non-fluorescent in character. Such blank microbeads thus will reflect and indicate the electronic "noise" of the flow cytometer, and thus permit the sensitivity of the instrument to be determined. When the sample to be measured by the flow cytometer is naturally fluorescent in character (e.g., due to the presence therein of indigenous riboflavin or other native fluorescent material), the population (a) microbeads will comprise microbeads which are fluorescently labeled with a first fluorescence component, to mimic the naturally occurring fluorescence of the autofluorescent sample as present before the autofluorescent sample is fluorescent dyed for measurement on the flow cytometer.

When the population (a) microbeads comprise autofluorescent microbeads, by virtue of incorporating fluorescence material (first fluorescence component) therein to simulate the fluorescence of the unstained autofluorescent sample, the same autofluorescence-simulating material must be incorporated in the population (b) microbeads, so that both microbead population (a) and (b) have the same "baseline" fluorescence characteristics, prior to fluorescent labeling of the population (b) microbeads with the fluorescent dye(s) which are utilized for staining the sample to be measured on the flow cytometer.

In this manner, both sets (a) and (b) of microbeads will possess the same intrinsic electronic noise and/or fluorescence characteristics.

The microbead standards employed in the alignment, compensation, and calibration kit of the invention are highly uniform, having a coefficient of variation (CV) of diameter which is $\leq 2\%$. Preferably, such microbead standards are of all the same size, in the range of the cells or particles to be measured, e.g., 2-20 microns in diameter, so as to fall within the forward and right angle dot plot range of the cell or particle samples being measured If calibration of sizing channels of the flow cytometer is desired, an additional series of microbeads of different calibrated size may be included in the kit to perform the appropriate calibrations, similar to those carried out for the fluorescence intensity channels.

The autofluorescent microbeads in the microbeads standards kit of the invention will not carry any fluorescent material other than the first fluorescence component which mimics the naturally occurring fluorescence of the sample to be measured on the flow cytometer. It is within the broad scope of the present invention, however to utilize a first fluorescence component which comprises a plurality of fluorescence species, as necessary to simulate the natural sample fluorescence.

As indicated hereinabove, there exist a variety of flow cytometry samples carrying varying amounts of indigenous fluorescent materials, e.g., biological cells containing riboflavin, which render the samples autofluorescent in character. Relatively high levels of autofluorescence have been observed in hepatic cells and in various cells in culture.

To facilitate the measurement of these autofluorescent samples, the microbead standards kit contains autofluorescent microbeads in population (a), and the population (b) microbeads, prior to being fluorescently labeled with the same dye(s) used to stain the samples for flow cytometer measurement, have a same fluorescence spectra and fluorescence intensity as the population (a) microbeads. Thus, the population (b) microbeads comprise the same first fluorescence component as the autofluorescent population (a) microbeads, with the population (b) microbeads being further fluorescently labeled with the dye(s) used to stain the samples, and with such staining dye(s) being different from the first fluorescence component.

In application to the measurement of autofluorescent samples, the autofluorescent microbead standard in the microbead standards kit must match the fluorescence spectra and intensity of the unlabeled (i.e., unstained) sample to be measured on the flow cytometer. Accordingly, the first fluorescence component is associated with otherwise "blank" microbeads in the population (a) microbeads referred to hereinabove, such that these microbeads containing the first fluorescent component match the excitation and emission spectra of the unlabeled autofluorescent samples.

In a further aspect of the microbead standards kit of the invention, in which the sensitivity of the various fluorescent channels of a flow cytometer is to be determined, a "blank" or non-fluorescent microbead is employed which does not carry any first fluorescent component or any other fluorescent markers or indicators, and whose material of composition is intrinsically non-fluorescent. Such blank microbead standard then is employed to indicate the level of electronic and optical "noise" in the flow cytometry system, as an indication of the sensitivity of the respective fluorescent channels of the flow cytometer. For such application, the population (b) microbeads carrying the additional fluorescent dye(s) used to stain the sample to be measured, likewise do not carry any first fluorescence component. Accordingly, the fluorescence levels of the population (b) microbeads in the secondary fluorescence channels of the flow cytometer will be attributable only to the fluorescent dyes with which such population (b) microbeads are labeled, and not to any autofluorescence-simulative material (first fluorescence component). Such a microbead standards kit, comprising a blank microbead standard population (a) and a set of otherwise blank microbeads which have been fluorescently labeled with the staining dye(s) employed to label the sample to be measured (population (b), provides both accurate compensation and a measure of the sensitivity of each fluorescent channel of the flow cytometer.

Apart from the blank and/or auto-fluorescent microbead standards described above, the microbead standards kit of the present invention comprises additional populations of microbeads which are fluorescently labeled with:

(1) at least two fluorescent dyes, so that such additional populations of microbeads will have excitation and emission spectra that match the spectra of the specific fluorescent dye(s) used to label the sample to be measured on the flow cytometer; and (2) the same first fluorescence component as the autofluorescent microbead standard, if the kit is to be employed to set up a flow cytometer for measuring an autofluorescent sample, and the kit comprises an autofluorescent microbead standard.

Each series of the additional populations of fluorescent microbead standards in the kit will be calibrated in terms of number of equivalent soluble fluorescent molecules of the particular dye. For example, if the samples to be measured are labeled with fluorescein- and phycoerythrin-conjugated antibodies, then a series of fluorescein microbead standards and a series of phycoerythrin microbead standards may be included in the kit. Preferably, the fluorescence intensity range of the microbeads will directly cover that of the samples to be measured, but the microbead standards kit may suitably contain microbeads with which the calibration may be extrapolated to cover the fluorescence intensity range of the sample.

The microbead standards kit of the present invention may also include fluorescent microbead standards which carry combinations of two or more of the dyes to be concurrently used to label the samples being measured. With proper compensation of the flow cytometer, such multilabeled microbeads will be detected in two or more of the respective primary fluorescence channels, so as to simulate individual multilabeled samples. The fluorescence intensities of the microbeads with respect to the individual dyes on the microbead may be selected and provided via appropriate dye incorporation techniques during the formation of the microbeads, so that their fluorescence intensities are equal or set to specific levels.

To perform accurate compensation adjustments on a flow cytometer employed to measure naturally fluorescent samples, then, two sources of fluorescence must be considered:

(1) fluorescence deriving from the fluorescent dyes which are used to label the sample, such as for example monoclonal antibody-conjugated dyes like fluorescein or phycoerythrin; and (2) the naturally occurring fluorescence, or auto fluorescence, of the sample itself, e.g., biological cell samples in which the cells contain naturally occurring fluorescent compounds such as riboflavin.

The autofluorescence of the sample must be taken into consideration when making the adjustment of the compensation circuits of the flow cytometer, so that the contribution from the sample autofluorescence to each of the fluorescence channels of the flow cytometer is not altered during the compensation procedure. This is accomplished in the practice of the present invention by adjusting the compensation circuits such that the level of fluorescence in the fluorescence channels, other than the channel designated for a particular fluorescent dye i.e., the primary channel, is equal to the level of autofluorescence of the sample prior to labeling the sample with fluorescent dyes.

In order to compensate a flow cytometer for measuring autofluorescent samples, by the use of microbeads, the microbeads must carry the same level of autofluorescence in all channels as the sample being measured on the flow cytometer. The microbeads must contain fluorescent constituents providing excitation and emission spectra which closely match the corresponding spectra resulting from the autofluorescence of the naturally fluorescent sample. In addition, the fluorescent microbead standards in the kit must produce spectra matching the spectra of the fluorescent dyes employed to label the naturally fluorescent sample.

In general, the foregoing criteria may be met in the practice of the present invention, as applied to a flow cytometer on which autofluorescent samples will be measured, by incorporating a first fluorescent component, e.g., fluorescent compound(s) or material(s), into all the microbeads to be employed in the kit, as a result of which the fluorescent properties of such microbeads closely match those of the naturally fluorescent sample, and then further labeling a selected portion of such microbeads with the same fluorescent dyes which are used to fluorescently label the naturally fluorescent sample.

By way of example, riboflavin as a first fluorescence component may be incorporated into a whole batch of microbeads at sufficient concentration to produce a fluorescence intensity matching that of the unlabeled, naturally fluorescent sample. Subsequently, one-third of the batch of microbeads carrying riboflavin is conjugated with fluorescein. Another one-third portion of the batch of microbeads carrying riboflavin is conjugated with phycoerythrin. The remaining one-third portion of the original batch is not further labeled with any fluorescent dyes, and contains as the only fluorescent constituent thereof the first fluorescence component, riboflavin. Accordingly, three microbead populations are produced, all of them containing the first fluorescence component, riboflavin, which mimics the naturally occurring fluorescence of the unlabeled naturally fluorescent sample. Using such populations to perform the compensation of the flow cytometer, only the fluorescence overlap due to the additional fluorescent dyes in each channel will be subtracted, and not the autofluorescence in each respective channel deriving from the first fluorescence component, riboflavin.

The preparation of a microbead standards kit according to the present invention for aligning, compensating, and/or calibrating a flow cytometer for measuring non-fluorescent samples, may be carried out in a manner similar to that generally described above in connection with the preparation of a microbead standards kit for flow cytometry measurement of autofluorescent samples, except that a first fluorescence component is of course not employed.

The method of use of the microbead standards kit of the invention thus involves three procedures to ensure that data from multi-fluorescent samples may be accurately obtained from a flow cytometer. These procedures are (i) alignment, (ii) compensation, and (iii) calibration. Although instruments from different flow cytometer manufacturers have their own peculiarities, the following description illustratively directed to the alignment, compensation, and calibration of a flow cytometer for measurement of autofluorescent samples, typifies the general approach to these procedures.

(1) Alignment of a Flow Cytometer

The flow cytometer may be aligned by first choosing the instrument parameters, e.g., excitation wavelength, emission barrier filters, amplifiers (linear or log), and signal gains to be used with the samples to be measured. One of the brightest fluorescent microbead standards thereupon is used to calibrate the first fluorescence channel F11 of the instrument. Adjustment of the various optical and electronic components of the flow cytometer then is carried out, as directed by the manufacturer, such that the instrument indicates maximum forward and right angle scatter and fluorescence channel F11 fluorescence intensities with the minimum distribution (% CV) for these microbeads, as measured on dot plots or histograms. Instrument components related to the additional fluorescence channels then may be aligned; this may be accomplished by adjusting the components of these channels to obtain a maximum intensity and minimum distribution while running bright microbeads carrying the dyes that will be used to calibrate those specific fluorescence channels.

(2) Multi-Channel Compensation of a Flow Cytometer

When two or more fluorescent dyes are simultaneously measured with a flow cytometer, the instrument must be compensated to remove spectral overlap in the secondary fluorescence channels. This is accomplished after the fluorescence channels of the instrument are aligned. The autofluorescent microbeads, matching the fluorescence spectra and intensity of the unlabeled, naturally fluorescent sample to be measured, then are run in the flow cytometer in the F11 versus F12 fluorescence channel dot plot or histogram display mode.

Since some microbeads have doublet and triplet components, which can confuse the analysis, gates (usually with the forward and side light scatter channels) are placed around the singlet microbead population such that only singlet microbeads register in the fluorescence channels. The PMT voltages and gains then are adjusted such that the signals in each of the fluorescence channels fall close to the origin of the fluorescence intensity measurement scales. Boundary levels may be set for each fluorescence channel such that any signals falling between zero and these levels will be considered non-fluorescent with respect to that particular fluorescence channel.

Next, there is added to the auto-fluorescent microbead population one or more of the fluorescent microbead populations in the calibration series, containing (1) the fluorescence component also present in the autofluorescent microbeads, to mimic the sample autofluorescence, and (2) the particular dyes that are used to label the naturally fluorescent sample to be measured. These additional microbeads will appear along the axis of their respective fluorescence channels and will spill over into areas of positive fluorescence in secondary channels. While running this mixture of microbeads, the compensation circuits of the instrument are turned on and adjusted, as prescribed by the manufacturer, such that the fluorescence signals in the secondary channels are moved between zero and the boundary level into the non-fluorescence region. An iterative procedure of PMT and compensation circuit adjustments may be required for optimal performance.

As a final check of the multi-channel compensation of the flow cytometer, microbeads carrying combinations of the dyes used to label the samples being measured may be run, to determine if they appear in both fluorescence channels as expected.

(3) Calibration of the Flow Cytometer

Figure 6:
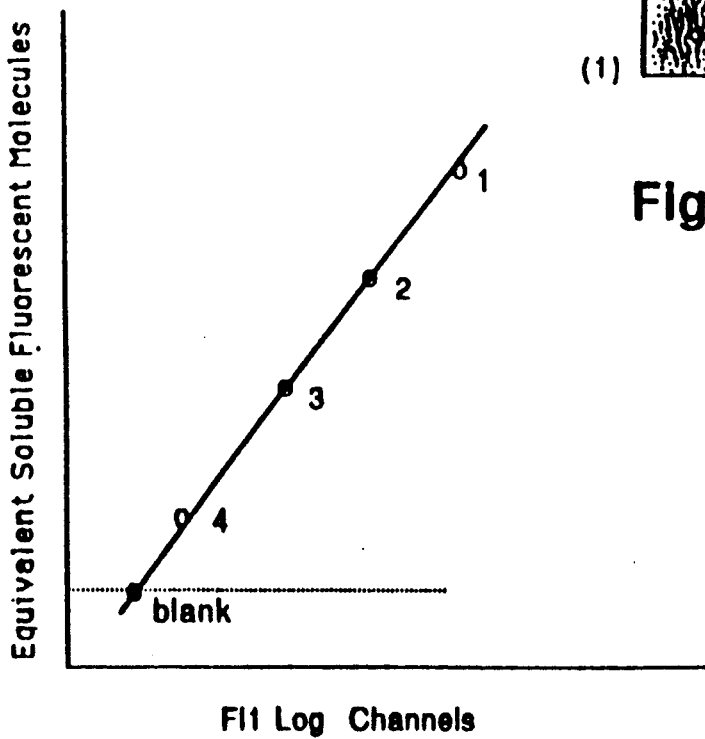
FIG. 6 is a calibration plot of the green fluorescence channel F11 of a flow cytometer, wherein numbers 1-5 indicate modal peak channels of microbead populations of decreasing fluorescence intensity, and the blank microbead indicates the sensitivity level of the instrument in that channel.

Once the alignment and compensation procedures are completed, the fluorescence channels may be calibrated using the series of microbead standards which carry the fluorescent dyes used to label the sample. Without changing any of the instrument settings, microbeads in each series are run separately, or as a mixture, and their peak modal medium or mean channels are plotted against the calibrated values of the fluorescence intensity for each microbead population in terms of number of equivalent soluble fluorescent molecules, to provide a calibration plot of the type shown in FIG. 6 hereof. When using a linear amplifier, the plot is made on log-log paper, and with a log amplifier, semi-log paper is used. The peak position of the blank microbeads on the calibration plot determines the threshold fluorescence above which the labeled sample may be measured for the particular fluorescence channel.

The features and advantages of the present invention are more fully shown with respect to the following non-limiting examples, wherein all parts and percentages are by weight, unless otherwise expressly stated.

EXAMPLE I

A population of microbead standards 5.5 microns in diameter and 1.5% coefficient of variation of diameter was synthesized containing 5% glycidyl methacrylate. A portion of these microbeads was impregnated with riboflavin in methanol solution (1% of saturation), to serve as autofluorescent microbeads simulating unlabeled autofluorescent cells.

Another portion of the microbeads were reacted at pH 9.5 with diaminopropane to provide primary amines with which to covalently bind fluorescein isothiocyanate (FITC). From these microbeads, four fluorescein microbead populations were labeled with increasing amounts of FITC.

Another portion of these glycidyl methacrylate microbeads was reacted with aqueous glycine solution at pH 9.5 to provide carboxyl groups with which to bind four different levels of phycoerythrin via carbodiimide activation. The detailed synthesis of these microbeads and their calibration in terms of equivalent soluble fluorescent molecules is described in U.S. Pat. No. 4,714,682.

A FACScan flow cytometer (Becton Dickinson & Co., Mountain View, California) was used having an air cooled argon laser tuned to an excitation wavelength of 488 nanometers (nm) and fitted with a 520-550 nm bandpass filter on the green fluorescence channel F11, and a 565 nm longpass barrier filter on the red fluorescence channel F12, with log amplifiers on the fluorescence channels. Count rates were kept to approximately 500 per second. The forward scatter, side scatter, and green F11 channels of the instrument were aligned using the brightest ($2.4 \times 10^5$ equivalent soluble fluorescent dye molecules per microbead) fluorescein (i.e., FITC labeled) microbead. The red F12 channel was then aligned with the brightest ($2.2 \times 10^5$ equivalent soluble fluorescent dye molecules per microbead) phycoerythrin microbead from Example I.

EXAMPLE III

After instrument alignment, as described in Example II, discrimination gates of the forward and side light scatter channels were set around the singlet peak of the autofluorescent microbeads from Example I (which matched the fluorescence properties of the unstained biological cells to be measured) and the flow cytometer was run with the voltages of the green F11 and red F12 PMT detectors adjusted so that the signals in the dot plot mode fell in the lower left hand corner of the dot plot.

Boundaries then were then set on the dot pattern generated with the autofluorescent microbeads, to demarcate regions below which non-fluorescent samples would be found equivalent to the autofluorescent blank microbeads.

The complete series of fluorescein and phycoerythrin microbead populations were next mixed with the autofluorescent blank microbeads and run. The resulting dot patterns indicated a small degree of fluorescent overlap of the phycoerythrin microbeads in the green F11 channel and a large degree of fluorescent overlap of the fluorescein microbeads in the red F12 channel. The instrument compensation circuits were turned on and adjusted (0.8 F11-%F12 and 24.7 F12-%F11) such that the fluorescence overlapping into secondary fluorescence channels was removed.

EXAMPLE IV

Without changing any settings on the FACScan ™ flow cytometer as set in Example III, the modal peaks of the histograms for each microbead population were plotted on semi-log paper for the respective fluorescence channels, since a log amplifier was used. The autofluorescent microbead standard was found to have a fluorescence intensity equivalent to 1,800 equivalent soluble fluorescein molecules in the green F11 channel and 2,400 equivalent soluble phycoerythrin molecules in the red F12 channel, indicating the level above which the cells being measured would show fluorescence labeling. Corresponding microbeads wholly devoid of any fluorescence components were found to have 750 equivalent soluble fluorescein molecules in the green F11 channel and 900 equivalent soluble phycoerythrin molecules in the red F12 channel, indicating the sensitivity of the instrument in those channels.

EXAMPLE V

A sample of normal whole blood drawn in ethylene diamine tetraacetate (EDTA) was stained with Leu 3-PE conjugated monoclonal antibody (directed against CD 4 T-cells) and Leu 2a-FITC conjugated monoclonal antibody (directed against CD 8 T-cells). The blood sample was lysed with a lysing reagent from Becton Dickinson to remove the erythrocytes before running on the FACScan ™ flow cytometer, and the lysate was washed once in phosphate buffer solution containing azide. The CD 4 cells were found to have a fluorescein intensity of 70,000 equivalent soluble fluorescent molecules per cell and the CD 8 cells were found to have a phycoerythrin intensity of 133,700 equivalent soluble fluorescent molecules per cell, as determined from the calibration plots of Example IV.

EXAMPLE VI

A batch of methyl methacrylate-glycidyl methacrylate microbeads 5.8 microns in diameter, synthesized as in the previous examples and containing surface epoxy functionality on the outer surfaces thereof, was washed three times in methanol and then suspended in a methanol solution of riboflavin (1 mg/ml) for 30 minutes at room temperature.

The microbeads then were removed from the riboflavin solution by centrifugation and washed four times in 0.1% sodium dodecylsulfate (SDS) and then washed in 50% methanolwater solution until the fluorescence intensity of the microbeads matched that of unlabeled human lymphocytes in both the green (fluorescein) and the red (phycoerythrin) fluorescence channels of the flow cytometer.

One-third of these beads incorporating riboflavin were placed in a 10% aqueous solution of 1,3-diaminopropane at pH 10.5 to convert the surface epoxy groups to corresponding carboxyl functionality on spacer arms, and the carboxyl groups then were activated with 1-ethyl-3-(3-dimethylaminopropyl) carbodiimide and linked to avidine which in turn bound biotinalated phycoerythrin.

The unlabeled riboflavin-incorporating microbeads were used to set the photomultiplier tubes (PMTs) of the fluorescence channels of the flow cytometer such that the microbeads appeared in the lower left quadrant of a dot plot display of the flow cytometer. Equal amounts of the fluorescein-labeled microbeads and phycoerythrin-labeled microbeads were mixed with the unlabeled microbeads and the levels of fluorescence in the secondary fluorescence channels were adjusted back to the autofluorescence level of the microbeads carrying only the riboflavin.

EXAMPLE VII

A batch of styrene-glycidyl methacrylate microbeads having a diameter of 6.1 microns was synthesized as in preceding examples. This batch of microbeads was washed three times in methanol and then suspended in a solution of methanol containing 1 mg/ml acridine orange and 1.3 mg/ml propidium iodide, for 20 minutes. The microbeads then were washed four times with 0.1% SDS solution followed by washes in 50% methanol-water, until the fluorescence levels in the green and red fluorescence channels of the flow cytometer matched the fluorescence intensity levels in the green and red channels of a different microbead population which contained unknown components but matched the auto-fluorescence intensity levels of human lymphocytes.

After washing the acridine orange/propidium iodide-containing microbeads with 0.1% SDS two additional times, one-third of the batch of microbeads was conjugated with fluorescein, and another one-third of the batch was conjugated with phycoerythrin, following which the microbeads were tested on a flow cytometer as in Example VI. The resulting levels of compensation were 29.3% compensation for the green channel and 0.8% compensation for the red channel. When human lymphocytes using CD 3 markers of fluorescein and phycoerythrin were run at these settings, the compensation was found to be accurate.

EXAMPLE VIII

This example is the same as Example VII, except that only the unlabeled microbeads were treated with acridine orange/propidium iodide. The fluorescein- and phycoerythrin-conjugated microbeads were labeled only with their respective dyes.

This set of microbead populations resulted in 38.3% compensation for the fluorescein channel and 0.1% compensation for the phycoerythrin channel. When human lymphocytes using CD 3 markers of fluorescein and phycoerythrin were run at these settings, it was found that the fluorescein channel was over-compensated, and the phycoerythrin channel was under-compensated.

EXAMPLE IX

This example, and the succeeding Example X below, demonstrate the feasibility of producing microbeads with covalently linked biotin to bind fluorescently labeled avidine compounds, simulating cells labeled with the same fluorescently labeled avidine compounds. Microbeads labeled in such manner are a superior standard for compensation adjustments, since the fluorescent dyes are the same in structure and binding to the microbeads (provided that the environment of the dyes is the same) as when such dyes are bound to cell samples.

Biotin microbeads were prepared by suspending methyl methacrylate-glycidyl methacrylate microbeads 9.5 microns in diameter, having primary amine groups on spacer arms attached to the surfaces of the microbeads, in a 0.05 M phosphate buffer solution at pH 7.2. To 50 milliliters of this solution, 25 milligrams of N-hydroxysuccinimidobiotin dissolved in two milliliters of dimethylformamide was added while stirring and allowed to react for one hour. The microbeads were washed three times in the same pH 7.2 buffer solution. StrepavidineFITC was added to the suspension, and the microbeads became highly fluorescent green under blue light excitation.

EXAMPLE X

To biotin microbeads prepared as in Example IX, avidine was added and the microbeads were washed three times with a buffer solution of the same type described in Example IX. Biotin-phycoerythrin was added while stirring the microbead suspension, resulting in bright fluorescent orange microbeads under blue light excitation.

EXAMPLE XI

Methyl methacrylate-glycidyl methacrylate microbeads were synthesized and maintained throughout the subsequent procedure devoid of any first fluorescence component. One-third of the batch of microbeads was labeled with fluorescein, and one-third of the batch was labeled with phycoerythrin, and the remaining one-third was not fluorescently labeled with any fluorescent dyes. The respective microbead populations were suspended in 0.05% bovine serum albumin and stored together When applied to the compensation of the flow cytometer, the compensation levels were measured as 0.8% for the phycoerythrin channel and 29.5% for the fluorescein channel.

After two weeks, the microbeads again were employed to compensate the flow cytometer. Compensation values in this second procedure were 2.8% compensation for the phycoerythrin channel and 12.0% for the fluorescein channel. Different PMT settings were observed for the blank beads, relative to the initial procedure, from which it was concluded that these beads had taken up some extraneous fluorescence components

EXAMPLE XII

The procedure of Example XI was repeated, but in the repeated procedure the mixed microbead populations were suspended in gelatin. Initially after their combination, the compensation values were the same as those initially determined in Example XI. After two weeks, the compensation values measured using the gelatin-suspended microbeads were essentially the same as the initial values, in both (phycoerythrin and fluorescein) channels.

From the comparative results of Examples XI and XII, it is concluded that suspension of the microbeads in gelatin-based media avoids the pick-up of extraneous dye molecules by the microbeads in the suspension, in contrast to other media such as the bovine serum albumin medium employed in Example XI.

Although riboflavin has been illustratively described herein as a first fluorescence component for labeling of microbeads to simulate the autofluorescence of naturally fluorescent samples, e.g., cells containing riboflavin, it will be apparent that the utility of the invention is not thus limited, and that any other suitable material may be employed as the first fluorescence component, depending on the microbead composition and the specific samples to be measured in a given application. Examples of other materials which may potentially be usefully employed as the first fluorescence components include acridine-orange and propidium iodide, as well as thiazole orange and propidium iodide.

In like manner, although the invention has been illustratively described herein primarily with respect to phycoerythrin and fluorescein as the dye species employed in the additional microbead populations in the microbead standards kit of the present invention, it will be apparent that numerous other dye species may be correspondingly employed, depending on the sample, flow cytometer, and microbeads involved in a specific application. Examples of other fluorescent dyes which may be potentially usefully employed in the broad practice of the invention include rhodamine derivatives such as tetramethylrhodamine isothiocyanate or Texas Red (rhodamine sulfonyl chloride), allophycocyanine, and phycobiliprotein derivatives.

While the invention has been described with reference to specific embodiments and compositions, it will be appreciated that numerous modifications, variations, and embodiments are possible, as being with the spirit and scope of the invention.

What is claimed is:

1. A microbead standards kit for alignment, compensation, and/or calibration of a flow cytometer, for use with a selected sample labeled with specific fluorescent dyes, said dyes selected from the group consisting of fluorescein, phycoerythrin, rhodamine derivative dyes, allophycocyanine and phycobiliprotein derivative dyes using multiple fluorescence channels of the flow cytometer, said kit comprising:
   (a) a first population of microbeads which are characterized by a same fluorescence spectra and fluorescence intensity as a selected naturally fluorescent sample, prior to the selected sample being labeled with at least two specific fluorescent dyes, said fluorescence spectra and fluorescence intensity of said first population being together termed underlying fluorescence characteristics;
   (b) at least two series of populations of microbeads which have the underlying fluorescence characteristics of said first population of microbeads (s), with each said series of microbeads being labeled with one of said specific dyes used to label the selected sample, such that each population of a series of microbeads is labeled with different amounts of the specific fluorescent dye, and has the fluorescence characteristics of spectra and intensity resulting from the combination of the underlying fluorescence of the microbeads and the specific fluorescence dye used to label the selected sample, said fluorescent dyes are selected from the group consisting of fluorescein, phycoerythrin, phycobiliprotein derivatives dyes;
   (c) said series of microbead populations (a) and (b) being constituted by highly uniform same sized microbeads having a coefficient of variation of diameter of about 2% or less; and
   (d) container means enclosing said microbead populations (a) and (b), wherein said populations of microbeads enable calibration and compensation of a flow cytometer.

2. A microbead standards kit according to claim 1, wherein said highly uniform same sized microbeads have a diameter in the range from about 2 to about 20 microns.

3. A microbead standards kit according to claim 1, wherein said first population of microbeads is constituted by autofluorescent microbeads, and each said series of microbead populations comprises said autofluorescent microbeads labeled with one of said specific fluorescent dye.

4. A microbead standards kit according to claim 1, wherein the microbeads of one said series of microbead populations are labeled to different intensities with one said specific fluorescent dyes, and the microbeads of the second series of microbead populations are labeled with a second of said specific fluorescent dye.

5. A microbead standards kit according to claim 1, wherein said at least two series comprises at least three series of microbead populations (b), with each population in a series labeled to a different intensity with on of said fluorescent dyes.

6. A microbead standards kit according to claim 4, wherein said first fluorescent dye is fluorescein, and said second fluorescent dye is phycoerythrin.

7. A microbead standards kit according to claim 5, wherein said different fluorescent dyes comprise fluorescein and phycoerythrin.

8. A microbead standards kit according to claim 4, wherein said first fluorescent dye is sulfonyl chloride derived from sulforhodamine 101, and said second fluorescent dye is allophycocyanine.

9. A microbead standards kit according to claim 6, wherein said different fluorescent dyes comprise a solfonyl chloride derived from sulforhodamine 101 and allophycocyanine.

10. A microbead standards kit according to claim 1, wherein said microbead populations (b) comprise microbeads having an avidine compound linked thereon, said avidine compound is linked to a biotinylated compound having said specific fluorescent dye linked thereon.

11. A microbead standards kit according to claim 10, wherein said avidine compounds are selected from a group consisting of avidine and strepavidine.

12. A microbead standards kit for alignment, compensation, and/or calibration of a flow cytometer, for use with a selected naturally fluorescent sample which is labeled with fluorescent dyes, said dyes selected from the group consisting of fluorescein, phycoerythrin, rhodamine derivative dyes, allophycocyanine and phycobiliprotein derivative dyes for measurement of the sample in multiple fluorescence channels of the flow cytometer, said kit comprising:

(a) a first population of microbeads which are fluorescently labeled with at least one fluorescent dyes such that said first population of microbeads is characterized by a same fluorescence spectra and fluorescence intensity as a selected naturally fluorescent sample being labeled with at least two specific fluorescent dyes, said fluorescence spectra and fluorescence intensity of said first population being together termed underlying fluorescence characteristics;

(b) at least two series of microbead populations which have the underlying fluorescence characteristics of said first fluorescence component with each said series of microbeads being labeled with one of said specific dyes used to label the selected sample, such that each population of a series of microbeads is labeled with different amount of the specific fluorescent dye, and has the fluorescence characteristics of spectra and intensity resulting from the combination of the underlying fluorescence of the microbeads and the specific fluorescence dye used to label the selected sample, said fluorescent dyes are selected from the group consisting of fluorescein, phycoerythrin, phycobiliprotein derivatives dyes;

(c) said microbead populations (a) and (b) being constituted by highly uniform same sized microbeads having a coefficient of variation of diameter of about 2% or less; and (d) container means enclosing said microbead populations (a) and (b), wherein said populations of microbeads enable calibration and compensation of a flow cytometer.

13. A microbead standards kit according to claim 12, wherein said first population of microbeads is labeled with riboflavin.

14. A microbead standards kit according to claim 12, wherein said first populations of microbeads is labeled with acridine orange and propidium iodide.

15. A microbead standards kit according to claim 12, wherein said first population of microbeads is labeled with thiazole orange and propidium iodide.

16. The flow cytometry microbead standards kit of claim 1, wherein said first population and said at least two or more population of microbeads are suspended in a gelatin-based medium in a container.

17. A method of aligning, compensating, and calibrating a flow cytometer comprising multiple fluorescence channels including F11 and F12 fluorescence channels, and forward and right angle scatter channels, a fluorescence excitation source, photomultiplier tubes and emission barrier filters for said multiple fluorescence channels, and amplifier and gain setting means, for subsequent measurement of a selected naturally fluorescent sample which is labeled with fluorescent dyes for measurement of the sample in said multiple fluorescence channels of the flow cytometer, said method comprising the steps of:

(i) providing a microbead standards kit comprising:
(a) a population of blank microbeads;
(b) a first population of microbeads which are characterized by a same fluorescence spectra and fluorescence intensity as a selected naturally fluorescent sample, prior to the selected naturally fluorescent sample being labeled with at least two specific fluorescent dyes, said fluorescence spectra and fluorescence intensity of said first population being together termed underlying fluorescence characteristics;

(c) at least two series of populations of microbeads which have the underlying fluorescence characteristics of said first population of microbeads, with each said series of microbeads being labeled with one of said specific dyes used to label said sample, such that each population of a series of microbeads is labeled with different amount of the specific fluorescent dye and has the fluorescence characteristics of spectra and intensity resulting from the combination of the underlying fluorescence of the microbeads and the specific fluorescence dye used to label the selected sample;

(d) said microbead populations (a), (b), and (c) being constituted by highly uniform same sized microbeads having a coefficient of diameter of about 2% or less, with said microbeads being substantially equivalent in size to said fluorescently labeled sample to be measured by said flow cytometer; and (e) container means enclosing said microbead populations (a), (b), and (c);

(ii) running an initial population series of fluorescent microbeads of said microbead population (c) detectable in an F11 fluorescence channel of said flow cytometer such that a dot plot or histogram resulting from said initial population of microbeads will have a maximum intensity and a minimum distribution i the forward and right angle scatter and F11 fluorescence channels;

(iii) repeating step (ii) with an additional microbead population series from said microbead population (c) labeled with a different fluorescent dye detectable in an F1 fluorescence channel of said flow cytometer;

(iv) running said microbead population (b) on said flow cytometer, and adjusting fluorescence channel PMT voltages and gains of said flow cytometer to position the resulting dot plot or histogram near the origin of the axis of each of the said fluorescence channels, and setting boundary levels in each said fluorescence channel to indicate fluorescence intensity of said microbead population (b);

(v) mixing said populations of fluorescent microbeads used in steps (ii) and (iii) with the microbead population (b) to form a fluorescent microbead adjustment mixture;

(vi) running the fluorescent microbead adjustment mixture on said flow cytometer and adjusting compensation circuits of said flow cytometer so that the fluorescence signal from each of the said microbead populations used in steps (ii) and (iii) registers as positive fluorescence in its respective primary fluorescent channel, and as non-fluorescent, matching the intensity level of said microbead population (b), in all other secondary fluorescent channels;

(vii) running microbead populations (c) on said flow cytometer, without changing any flow cytometer settings, to determine a peak channel of a series of microbead populations labeled with said fluorescent dyes at varying specific levels of fluorescence intensity;

(viii) constructing a calibration plot of equivalent soluble fluorescence dye molecules per microbead as a function of fluorescence intensity channel of said flow cytometer;

(ix) running said blank microbead population (a) on said flow cytometer and determining the position of a peak channel thereof for each said fluorescent channel to determine the sensitivity of each said fluorescent channel of said flow cytometer; and (x) determining on said calibarion plot the position of the peak channel of said blank microbead population (a) for each said fluorescent channel to indicate the threshold above which fluorescence intensity of said selected fluorescently labeled sample may be measured by the said fluorescence channels of said flow cytometer, wherein said populations of microbeads enable calibration, alignment, and compensation of a flow cytometer.

18. A method according to claim 17, comprising repeating step (ii) for each of said fluorescent channels of said flow cytometer.

19. A method according to claim 17, further comprising running on said flow cytometer microbead populations (c) comprising microbeads each of which is labeled with at least two fluorescent dyes, to confirm capability of said flow cytometer for simultaneous fluorescence detection for said selected fluorescently labeled sample labeled with a corresponding combination of said fluorescent dyes.

20. A method according to claim 17, wherein said fluorescent dye comprises at least one member of the group consisting of fluorescein, phycoerythrin a sulfonyl chloride derived from sulforhodamine 101, and allophycocyanine.

21. A method according to claim 17, wherein said first fluorescence component is riboflavin.

22. A method according to claim 17, wherein said first fluorescence component is acridine orange and propidium iodide.

23. A method according to claim 17, wherein said first fluorescence component is thiazole orange and propidium iodide.

24. A method according to claim 17, comprising constructing said calibration plot as a log-log plot, wherein said amplifier means of said flow cytometer is a linear amplifier.

25. A method according to claim 17, wherein said calibration plot is constructed as a semi-log plot, and said amplifier means of said flow cytometer is a log amplifier.

26. A method of analyzing a selected cellular or particulate sample on a flow cytometer, comprising measuring said sample on said flow cytometer after said flow cytometer has been aligned, compensated, and calibrated in accordance with the method of 17.

27. A method according to claim 26, wherein said sample comprises T-cells.

28. A method according to claim 27, wherein said T-cells are stained with fluorescein isothiocyanate and phycoerythrin.

29. A method according to claim 28, wherein said T-cells are stained with said fluorescent dyes conjugated with monoclonal antibodies to said T-cells.

* * * * *